US009176141B2

(12) United States Patent
Al-Ali et al.

(10) Patent No.: US 9,176,141 B2
(45) Date of Patent: Nov. 3, 2015

(54) PHYSIOLOGICAL MONITOR CALIBRATION SYSTEM

(75) Inventors: Ammar Al-Ali, Tustin, CA (US); Massi Joe E. Kiani, Laguna Niguel, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 798 days.

(21) Appl. No.: 13/274,306

(22) Filed: Oct. 15, 2011

(65) Prior Publication Data

US 2012/0116175 A1 May 10, 2012

Related U.S. Application Data

(63) Continuation-in-part of application No. 11/746,451, filed on May 9, 2007, now Pat. No. 8,998,809.

(60) Provisional application No. 61/393,551, filed on Oct. 15, 2010, provisional application No. 60/800,512, filed on May 15, 2006.

(51) Int. Cl.

| | |
|---|---|
| ***A61B 5/05*** | (2006.01) |
| ***G01N 33/66*** | (2006.01) |
| ***A61B 5/145*** | (2006.01) |
| ***A61B 5/1495*** | (2006.01) |
| ***G06F 19/00*** | (2011.01) |
| *A61B 5/1459* | (2006.01) |
| *A61B 5/00* | (2006.01) |

(52) U.S. Cl.

CPC .............. *G01N 33/66* (2013.01); *A61B 5/1495* (2013.01); *A61B 5/14542* (2013.01); *G06F 19/3412* (2013.01); *A61B 5/1459* (2013.01); *A61B 5/14532* (2013.01); *A61B 5/7275* (2013.01); *A61B 2560/0223* (2013.01); *A61B 2562/0295* (2013.01); *G06F 19/3468* (2013.01)

(58) Field of Classification Search

USPC .......................................... 600/345–347, 365

See application file for complete search history.

(56) References Cited

U.S. PATENT DOCUMENTS

| | | | |
|---|---|---|---|
| 4,960,128 | A | 10/1990 | Gordon et al. |
| 4,964,408 | A | 10/1990 | Hink et al. |
| 5,041,187 | A | 8/1991 | Hink et al. |
| 5,069,213 | A | 12/1991 | Polczynski |
| 5,163,438 | A | 11/1992 | Gordon et al. |

(Continued)

FOREIGN PATENT DOCUMENTS

WO WO 2012/075322 6/2012

OTHER PUBLICATIONS

Smith, "The Pursuit of Noninvasive Glucose: Hunting the Deceitful Turkey", Retrieved from http://www.mendosa.com/noninvasive_gluclose.pdf (retrieved on Jan. 3, 2013) pp. i-129 (2006).

(Continued)

*Primary Examiner* — Michael D'Angelo
(74) *Attorney, Agent, or Firm* — Knobbe, Martens, Olson & Bear, LLP

(57) ABSTRACT

A calibration system is disclosed for calibrating a first physiological monitoring device using a second physiological monitoring device. The first physiological monitor measures a first indication of a physiological parameter. The second physiological monitor measures a second indication of the physiological parameter. The first and second indications are used to calibrate the first physiological monitoring device.

14 Claims, 13 Drawing Sheets

(56) References Cited

U.S. PATENT DOCUMENTS 5,319,355 A 6/1994 Russek
5,337,744 A 8/1994 Branigan
5,341,805 A 8/1994 Stavridi et al.
D353,195 S 12/1994 Savage et al.
D353,196 S 12/1994 Savage et al.
5,377,676 A 1/1995 Vari et al.
D359,546 S 6/1995 Savage
5,431,170 A 7/1995 Mathews
D361,840 S 8/1995 Savage et al.
D362,063 S 9/1995 Savage et al.
5,452,717 A 9/1995 Branigan et al.
D363,120 S 10/1995 Savage et al.
5,456,252 A 10/1995 Vari et al.
5,479,934 A 1/1996 Imran
5,482,036 A 1/1996 Diab et al.
5,490,505 A 2/1996 Diab et al.
5,494,043 A 2/1996 O'Sullivan et al.
5,505,828 A 4/1996 Wong et al.
5,533,511 A 7/1996 Kaspari et al.
5,534,851 A 7/1996 Russek
5,561,275 A 10/1996 Savage et al.
5,562,002 A 10/1996 Lalin
5,590,649 A 1/1997 Caro et al.
5,602,924 A 2/1997 Durand et al.
5,632,272 A 5/1997 Diab et al.
5,638,816 A 6/1997 Kiani-Azarbayjany et al.
5,638,818 A 6/1997 Diab et al.
5,645,440 A 7/1997 Tobler et al.
5,685,299 A 11/1997 Diab et al.
D393,830 S 4/1998 Tobler et al.
5,743,262 A 4/1998 Lepper, Jr. et al.
5,758,644 A 6/1998 Diab et al.
5,760,910 A 6/1998 Lepper, Jr. et al.
5,769,785 A 6/1998 Diab et al.
5,782,757 A 7/1998 Diab et al.
5,785,659 A 7/1998 Caro et al.
5,791,347 A 8/1998 Flaherty et al.
5,810,734 A 9/1998 Caro et al.
5,823,950 A 10/1998 Diab et al.
5,830,131 A 11/1998 Caro et al.
5,833,618 A 11/1998 Caro et al.
5,860,919 A 1/1999 Kiani-Azarbayjany et al.
5,890,929 A 4/1999 Mills et al.
5,904,654 A 5/1999 Wohltmann et al.
5,919,134 A 7/1999 Diab
5,934,925 A 8/1999 Tobler et al.
5,940,182 A 8/1999 Lepper, Jr. et al.
5,995,855 A 11/1999 Kiani et al.
5,997,343 A 12/1999 Mills et al.
6,002,952 A 12/1999 Diab et al.
6,011,986 A 1/2000 Diab et al.
6,027,452 A 2/2000 Flaherty et al.
6,036,642 A 3/2000 Diab et al.
6,045,509 A 4/2000 Caro et al.
6,067,462 A 5/2000 Diab et al.
6,081,735 A 6/2000 Diab et al.
6,088,607 A 7/2000 Diab et al.
6,110,522 A 8/2000 Lepper, Jr. et al.
6,124,597 A 9/2000 Shehada et al.
6,128,521 A 10/2000 Marro et al.
6,129,675 A 10/2000 Jay
6,144,868 A 11/2000 Parker
6,151,516 A 11/2000 Kiani-Azarbayjany et al.
6,152,754 A 11/2000 Gerhardt et al.
6,157,850 A 12/2000 Diab et al.
6,165,005 A 12/2000 Mills et al.
6,184,521 B1 2/2001 Coffin, IV et al.
6,206,830 B1 3/2001 Diab et al.
6,229,856 B1 5/2001 Diab et al.
6,232,609 B1 5/2001 Snyder et al.
6,236,872 B1 5/2001 Diab et al.
6,241,683 B1 6/2001 Macklem et al.
6,253,097 B1 6/2001 Aronow et al.
6,256,523 B1 7/2001 Diab et al.
6,263,222 B1 7/2001 Diab et al.
6,278,522 B1 8/2001 Lepper, Jr. et al.
6,280,213 B1 8/2001 Tobler et al.
6,285,896 B1 9/2001 Tobler et al.
6,301,493 B1 10/2001 Marro et al.
6,317,627 B1 11/2001 Ennen et al.
6,321,100 B1 11/2001 Parker
6,325,761 B1 12/2001 Jay
6,334,065 B1 12/2001 Al-Ali et al.
6,343,224 B1 1/2002 Parker
6,349,228 B1 2/2002 Kiani et al.
6,360,114 B1 3/2002 Diab et al.
6,368,283 B1 4/2002 Xu et al.
6,371,921 B1 4/2002 Caro et al.
6,377,829 B1 4/2002 Al-Ali
6,388,240 B2 5/2002 Schulz et al.
6,397,091 B2 5/2002 Diab et al.
6,430,437 B1 8/2002 Marro
6,430,525 B1 8/2002 Weber et al.
6,463,311 B1 10/2002 Diab
6,470,199 B1 10/2002 Kopotic et al.
6,501,975 B2 12/2002 Diab et al.
6,505,059 B1 1/2003 Kollias et al.
6,515,273 B2 2/2003 Al-Ali
6,519,487 B1 2/2003 Parker
6,522,903 B1 2/2003 Berman et al.
6,525,386 B1 2/2003 Mills et al.
6,526,300 B1 2/2003 Kiani et al.
6,541,756 B2 4/2003 Schulz et al.
6,542,764 B1 4/2003 Al-Ali et al.
6,580,086 B1 6/2003 Schulz et al.
6,584,336 B1 6/2003 Ali et al.
6,595,316 B2 7/2003 Cybulski et al.
6,597,932 B2 7/2003 Tian et al.
6,597,933 B2 7/2003 Kiani et al.
6,606,511 B1 8/2003 Ali et al.
6,632,181 B2 10/2003 Flaherty et al.
6,639,668 B1 10/2003 Trepagnier
6,640,116 B2 10/2003 Diab
6,643,530 B2 11/2003 Diab et al.
6,650,917 B2 11/2003 Diab et al.
6,654,624 B2 11/2003 Diab et al.
6,658,276 B2 12/2003 Pishney et al.
6,661,161 B1 12/2003 Lanzo et al.
6,671,531 B2 12/2003 Al-Ali et al.
6,678,543 B2 1/2004 Diab et al.
6,684,090 B2 1/2004 Ali et al.
6,684,091 B2 1/2004 Parker
6,697,656 B1 2/2004 Al-Ali
6,697,657 B1 2/2004 Shehada et al.
6,697,658 B2 2/2004 Al-Ali
RE38,476 E 3/2004 Diab et al.
6,699,194 B1 3/2004 Diab et al.
6,714,804 B2 3/2004 Al-Ali et al.
RE38,492 E 4/2004 Diab et al.
6,721,582 B2 4/2004 Trepagnier et al.
6,721,585 B1 4/2004 Parker
6,725,075 B2 4/2004 Al-Ali
6,728,560 B2 4/2004 Kollias et al.
6,735,459 B2 5/2004 Parker
6,745,060 B2 6/2004 Diab et al.
6,760,607 B2 7/2004 Al-All
6,770,028 B1 8/2004 Ali et al.
6,771,994 B2 8/2004 Kiani et al.
6,792,300 B1 9/2004 Diab et al.
6,813,511 B2 11/2004 Diab et al.
6,816,741 B2 11/2004 Diab
6,822,564 B2 11/2004 Al-Ali
6,826,419 B2 11/2004 Diab et al.
6,830,711 B2 12/2004 Mills et al.
6,850,787 B2 2/2005 Weber et al.
6,850,788 B2 2/2005 Al-Ali
6,852,083 B2 2/2005 Caro et al.
6,861,639 B2 3/2005 Al-Ali
6,898,452 B2 5/2005 Al-Ali et al.
6,920,345 B2 7/2005 Al-Ali et al.
6,931,268 B1 8/2005 Kiani-Azarbayjany et al.
6,934,570 B2 8/2005 Kiani et al.
6,939,305 B2 9/2005 Flaherty et al.
6,943,348 B1 9/2005 Coffin, IV

(56) References Cited

U.S. PATENT DOCUMENTS 6,950,687 B2 9/2005 Al-Ali
6,961,598 B2 11/2005 Diab
6,970,792 B1 11/2005 Diab
6,979,812 B2 12/2005 Al-Ali
6,985,764 B2 1/2006 Mason et al.
6,993,371 B2 1/2006 Kiani et al.
6,996,427 B2 2/2006 Ali et al.
6,999,904 B2 2/2006 Weber et al.
7,003,338 B2 2/2006 Weber et al.
7,003,339 B2 2/2006 Diab et al.
7,015,451 B2 3/2006 Dalke et al.
7,024,233 B2 4/2006 Ali et al.
7,027,849 B2 4/2006 Al-Ali
7,030,749 B2 4/2006 Al-Ali
7,039,449 B2 5/2006 Al-Ali
7,041,060 B2 5/2006 Flaherty et al.
7,044,918 B2 5/2006 Diab
7,067,893 B2 6/2006 Mills et al.
7,096,052 B2 8/2006 Mason et al.
7,096,054 B2 8/2006 Abdul-Hafiz et al.
7,132,641 B2 11/2006 Schulz et al.
7,142,901 B2 11/2006 Kiani et al.
7,149,561 B2 12/2006 Diab
7,186,966 B2 3/2007 Al-Ali
7,190,261 B2 3/2007 Al-Ali
7,215,984 B2 5/2007 Diab
7,215,986 B2 5/2007 Diab
7,221,971 B2 5/2007 Diab
7,225,006 B2 5/2007 Al-Ali et al.
7,225,007 B2 5/2007 Al-Ali
RE39,672 E 6/2007 Shehada et al.
7,239,905 B2 7/2007 Kiani-Azarbayjany et al.
7,245,953 B1 7/2007 Parker
7,254,429 B2 8/2007 Schurman et al.
7,254,431 B2 8/2007 Al-Ali
7,254,433 B2 8/2007 Diab et al.
7,254,434 B2 8/2007 Schulz et al.
7,272,425 B2 9/2007 Al-Ali
7,274,955 B2 9/2007 Kiani et al.
D554,263 S 10/2007 Al-Ali
7,280,858 B2 10/2007 Al-Ali et al.
7,289,835 B2 10/2007 Mansfield et al.
7,292,883 B2 11/2007 De Felice et al.
7,295,866 B2 11/2007 Al-Ali
7,328,053 B1 2/2008 Diab et al.
7,332,784 B2 2/2008 Mills et al.
7,340,287 B2 3/2008 Mason et al.
7,341,559 B2 3/2008 Schulz et al.
7,343,186 B2 3/2008 Lamego et al.
D566,282 S 4/2008 Al-Ali et al.
7,355,512 B1 4/2008 Al-Ali
7,356,365 B2 4/2008 Schurman
7,371,981 B2 5/2008 Abdul-Hafiz
7,373,193 B2 5/2008 Al-Ali et al.
7,373,194 B2 5/2008 Weber et al.
7,376,453 B1 5/2008 Diab et al.
7,377,794 B2 5/2008 Al-Ali et al.
7,377,899 B2 5/2008 Weber et al.
7,383,070 B2 6/2008 Diab et al.
7,415,297 B2 8/2008 Al-Ali et al.
7,428,432 B2 9/2008 Ali et al.
7,438,683 B2 10/2008 Al-Ali et al.
7,440,787 B2 10/2008 Diab
7,454,240 B2 11/2008 Diab et al.
7,467,002 B2 12/2008 Weber et al.
7,469,157 B2 12/2008 Diab et al.
7,471,969 B2 12/2008 Diab et al.
7,471,971 B2 12/2008 Diab et al.
7,483,729 B2 1/2009 Al-Ali et al.
7,483,730 B2 1/2009 Diab et al.
7,489,958 B2 2/2009 Diab et al.
7,496,391 B2 2/2009 Diab et al.
7,496,393 B2 2/2009 Diab et al.
D587,657 S 3/2009 Al-Ali et al.
7,499,741 B2 3/2009 Diab et al.
7,499,835 B2 3/2009 Weber et al.
7,500,950 B2 3/2009 Al-Ali et al.
7,509,154 B2 3/2009 Diab et al.
7,509,494 B2 3/2009 Al-Ali
7,510,849 B2 3/2009 Schurman et al.
7,526,328 B2 4/2009 Diab et al.
7,530,942 B1 5/2009 Diab
7,530,949 B2 5/2009 Al Ali et al.
7,530,955 B2 5/2009 Diab et al.
7,563,110 B2 7/2009 Al-Ali et al.
7,596,398 B2 9/2009 Al-Ali et al.
7,618,375 B2 11/2009 Flaherty et al.
D606,659 S 12/2009 Kiani et al.
7,647,083 B2 1/2010 Al-Ali et al.
D609,193 S 2/2010 Al-Ali et al.
D614,305 S 4/2010 Al-Ali et al.
RE41,317 E 5/2010 Parker
7,729,733 B2 6/2010 Al-Ali et al.
7,734,320 B2 6/2010 Al-Ali
7,761,127 B2 7/2010 Al-Ali et al.
7,761,128 B2 7/2010 Al-Ali et al.
7,764,982 B2 7/2010 Dalke et al.
D621,516 S 8/2010 Kiani et al.
7,791,155 B2 9/2010 Diab
7,801,581 B2 9/2010 Diab
7,822,452 B2 10/2010 Schurman et al.
RE41,912 E 11/2010 Parker
7,844,313 B2 11/2010 Kiani et al.
7,844,314 B2 11/2010 Al-Ali
7,844,315 B2 11/2010 Al-Ali
7,865,222 B2 1/2011 Weber et al.
7,873,497 B2 1/2011 Weber et al.
7,880,606 B2 2/2011 Al-Ali
7,880,626 B2 2/2011 Al-Ali et al.
7,891,355 B2 2/2011 Al-Ali et al.
7,894,868 B2 2/2011 Al-Ali et al.
7,899,507 B2 3/2011 Al-Ali et al.
7,899,518 B2 3/2011 Trepagnier et al.
7,904,132 B2 3/2011 Weber et al.
7,909,772 B2 3/2011 Popov et al.
7,910,875 B2 3/2011 Al-Ali
7,919,713 B2 4/2011 Al-Ali et al.
7,937,128 B2 5/2011 Al-Ali
7,937,129 B2 5/2011 Mason et al.
7,937,130 B2 5/2011 Diab et al.
7,941,199 B2 5/2011 Kiani
7,951,086 B2 5/2011 Flaherty et al.
7,957,780 B2 6/2011 Lamego et al.
7,962,188 B2 6/2011 Kiani et al.
7,962,190 B1 6/2011 Diab et al.
7,976,472 B2 7/2011 Kiani
7,988,637 B2 8/2011 Diab
7,990,382 B2 8/2011 Kiani
7,991,446 B2 8/2011 Al-Ali et al.
8,000,761 B2 8/2011 Al-Ali
8,008,088 B2 8/2011 Bellott et al.
RE42,753 E 9/2011 Kiani-Azarbayjany et al.
8,019,400 B2 9/2011 Diab et al.
8,028,701 B2 10/2011 Al-Ali et al.
8,029,765 B2 10/2011 Bellott et al.
8,036,728 B2 10/2011 Diab et al.
2003/0130616 A1 7/2003 Steil et al.
2005/0203360 A1* 9/2005 Brauker et al. ............... 600/345
2006/0020192 A1 1/2006 Brister et al.
2006/0229531 A1 10/2006 Goldberger et al.
2007/0265514 A1 11/2007 Kiani
2010/0099964 A1 4/2010 O'Reilly et al.
2010/0168537 A1 7/2010 Ueda et al.

OTHER PUBLICATIONS

International Search Report and Written Opinion issued in application No. PCT/US2012/060074 on Jan. 11, 2013.

* cited by examiner 400
407
405
401
Reliable Glucose Monitor
301
Minimally Invasive Glucose Monitor
403
303
409
411
300

Minimally Invasive Glucose Monitor
301
423
303
300

PHYSIOLOGICAL MONITOR CALIBRATION SYSTEM

RELATED APPLICATIONS

This application claims priority under 35 U.S.C. §119(e) as a nonprovisional of to U.S. Provisional Application No. 61/393,551, filed Oct. 15, 2010, titled "Physiological Monitor Calibration System," the disclosure of which is hereby incorporated by reference in its entirety. This application also claims priority under 35 U.S.C. §120 as a continuation-in-part of U.S. application Ser. No. 11/746,451, filed May 9, 2007, titled "Systems and Methods for Calibrating Minimally Invasive and Non-Invasive Physiological Sensor Devices," the disclosure of which is hereby incorporated by reference in its entirety.

BACKGROUND

Diabetes is a common cause of kidney disease, blindness among adults under the age of 65, and limb amputation. The effects of diabetes can be greatly reduced, if not eliminated all together, with proper monitoring of blood glucose. Many glucose monitors in use today require that a person be pricked with a sharp object in order to draw a small amount of blood to test for glucose levels. This process of measuring blood is often painful and uncomfortable. Although minimally and non-invasive blood glucose systems are being developed, they generally suffer from signal processing challenges affecting accuracy. One common challenge of minimally invasive glucose monitoring systems is referred to as drift. Drift generally occurs during the first few hours or days that a minimally invasive monitor's probe is inserted in the body and may cause inaccuracies.

SUMMARY

Aspects of the present disclosure include systems and methods for calibrating minimally invasive and non-invasive physiological sensor devices. The calibration is used to improve accuracy. In some embodiments, when the system begins taking measurements, the system may experience drift. FIG. 1 illustrates a graph 100 of glucose levels 101 in a patient vs. measured glucose 103 measured by a minimally invasive glucose monitor affected by drift. As illustrated, for a period of time, referred to herein as the calibration period, the measured glucose is less accurate due to, for example, drift. In minimally invasive systems, drift may be caused by protein buildup on the implanted device. In other systems, drift or other inaccuracies may be caused by any number of other issues known to an artisan from the disclosure herein. As with all patient monitors, more accurate and more reliable systems are preferred.

In an embodiment, a minimally invasive glucose monitor is described. The minimally invasive glucose monitor includes a probe which is inserted into a patient. The probe nearly continuously measures the patient's glucose levels and reports glucose information to the minimally invasive glucose monitor. The minimally invasive glucose monitor also includes a calibration input for receiving glucose information about the patient derived from a reliable glucose monitor. The glucose information received from the reliable glucose monitor is used to calibrate the minimally invasive glucose monitor. The minimally invasive glucose monitor may also include one or more outputs for outputting glucose and calibration related information. The inputs and outputs can be wired or wireless.

Although described with respect to glucose monitoring, a person of skill in the art will recognize that the present calibration system can be used to monitor and calibrate other physiological parameters, such as, for example, blood oxygen levels, blood carbon monoxide levels, blood pH levels, methemoglobin levels, pulse rates, trend or physiological traces, or any other physiological parameter. In addition, although described with respect to a minimally invasive patient monitor, the present disclosure is also applicable to the calibration of both invasive and non-invasive patient monitors.

In an embodiment, a method of calibrating a glucose measurement device is disclosed. The method includes acquiring a first indication of a glucose measurement from a first device, acquiring a second indication of a glucose measurement from a second device, and calibrating the second device using the first indication from the first device and the second indication from the second device. In an embodiment, the first and second devices comprise patient monitors. In an embodiment, the first and second devices are operably connected to the same patient. In an embodiment, the first and second indications are obtained at substantially the same time. In an embodiment, calibration comprises one or more of modeling, scaling, transforming, finding a best fit, finding a linear fit, filtering, adaptive correlation, and cross correlation. In an embodiment, the first device comprises an invasive physiological measurement device. In an embodiment, the second device comprises a minimally invasive physiological measurement device. In an embodiment, the second device comprises a non invasive physiological measurement device.

In an embodiment, a method of calibrating a physiological measurement device is disclosed. The method includes acquiring a first indication of one or more physiological measurements from a first device, acquiring a second indication of the one or more physiological measurements from a second device, and calibrating the second device using the first indication from the first device and the second indication from the second device. In an embodiment, the first and second devices comprise patient monitors. In an embodiment, the first and second devices are operably connected to the same patient. In an embodiment, the first and second indications are obtained at substantially the same time. In an embodiment, calibration comprises one or more of modeling, scaling, transforming, finding a best fit, finding a linear fit, filtering, adaptive correlation, and cross correlation. In an embodiment, the one or more physiological parameters comprise one or more of glucose, blood oxygen, pH, blood carbon monoxide levels, and methemoglobin. In an embodiment, the first device comprises an invasive physiological measurement device. In an embodiment, the second device comprises a minimally invasive physiological measurement device. In an embodiment, the second device comprises a non invasive physiological measurement device.

In an embodiment, a calibration system for calibrating a physiological measurement monitor is disclosed. The calibration system includes a first physiological monitor, a calibration module including a first input for inputting measured physiological data and a second input for inputting reliable data indicative of one or more physiological parameters. The calibration module is configured to calibrate the first physiological monitor using the information inputted over the first and second inputs. In an embodiment, the calibration system also includes a second physiological monitor for measuring the reliable data indicative of one or more physiological parameters. In an embodiment, the second physiological monitor comprises an invasive physiological measurement device. In an embodiment, the first physiological monitor comprises a minimally invasive physiological measurement device. In an embodiment, the first physiological monitor comprises a non invasive physiological measurement device. In an embodiment, the calibration system also includes one or more signal outputs. In an embodiment, the one or more signal outputs comprise a display output. In an embodiment, the one or more signal outputs comprise a trend output. In an embodiment, the one or more signal outputs comprise a waveform output. In an embodiment, the waveform output comprises a synthesized waveform. In an embodiment, the waveform output comprises a scaled waveform. In an embodiment, the one or more signal outputs comprise an error output.

In an embodiment, a method of calibrating a physiological measurement device is disclosed. The method of calibrating a physiological measurement includes acquiring a first indication of a glucose measurement from a first device, acquiring a second indication of a glucose measurement from a second device, and comparing the first indication and the second indication. Based on the comparison of the first indication and the second indication, if the first and second indications are not the same or close, the method also includes calibrating the second device using the first indication from the first device and the second indication from the second device, waiting an amount of time and requiring the first and second indications, comparing the reacquired first and second indications, and based on the comparison of the reacquired first and second indications, recalibrating the second device using the reacquired first and second indications.

In an embodiment, the amount of time comprises a predetermined amount of time. In an embodiment, the amount of time comprises about 5 minutes or less to about 12 hours or more. In an embodiment, the predetermined amount of time comprises about 5 minutes to about 10 minutes. In an embodiment, the predetermined amount of time comprises about 1 hour to about 2 hours. In an embodiment, the method also includes dynamically determining the amount of time. In an embodiment, dynamically determining comprises determining an amount of time based on the comparison of the first and second indications. In an embodiment, dynamically determining comprises determining an amount of time based on the comparison of the reacquired first and second indications.

BRIEF DESCRIPTION OF THE DRAWINGS

The drawings and the associated descriptions are provided to illustrate embodiments of the disclosure and not to limit the scope of the claims.

DETAILED DESCRIPTION

Embodiments of the present disclosure include systems and methods for calibrating a physiological monitoring device. A reliable, often invasive, method of measuring a physiological parameter is used to calibrate measurements of a minimally invasive or non-invasive physiological measurement device. In an embodiment, the reliable monitor and the minimally invasive or non-invasive monitor measure the same physiological parameter from the same patient within a time period deemed appropriate. In an embodiment, a patient can be set up with a long term, minimally invasive physiological measurement device with minimized discomfort during the initialization period. In an embodiment, a patient can use a minimally invasive physiological measurement device to continuously measure a physiological parameter, using an invasive measurement device periodically to calibrate the minimally invasive physiological measurement device. In an embodiment, the physiological parameter is one or more of glucose, blood oxygen, pH, blood carbon monoxide levels, and methemoglobin.

Figure 1:
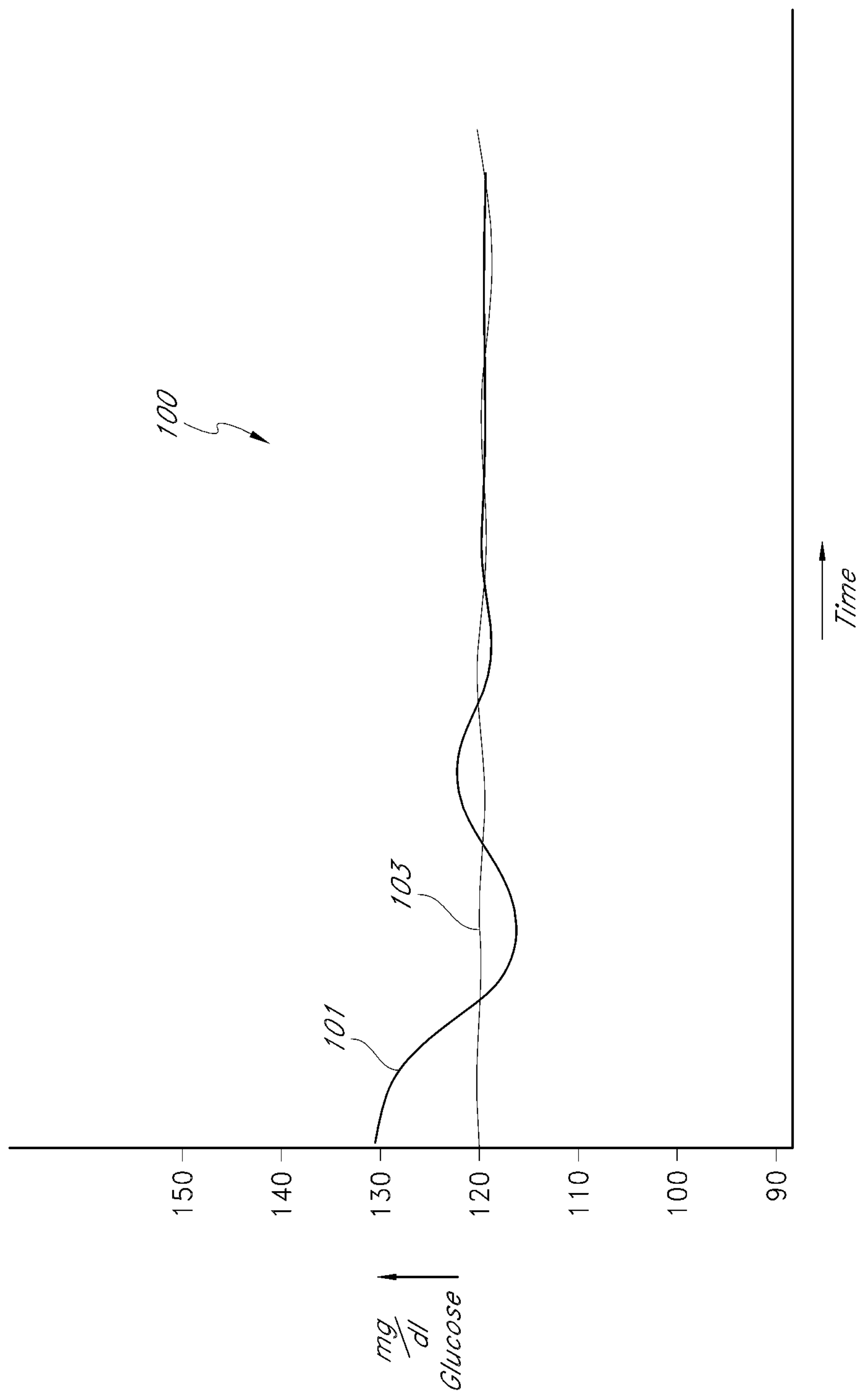
FIG. 1 illustrates a graph of actual glucose v. measured glucose for a glucose monitor experiencing drift.
Figure 2:
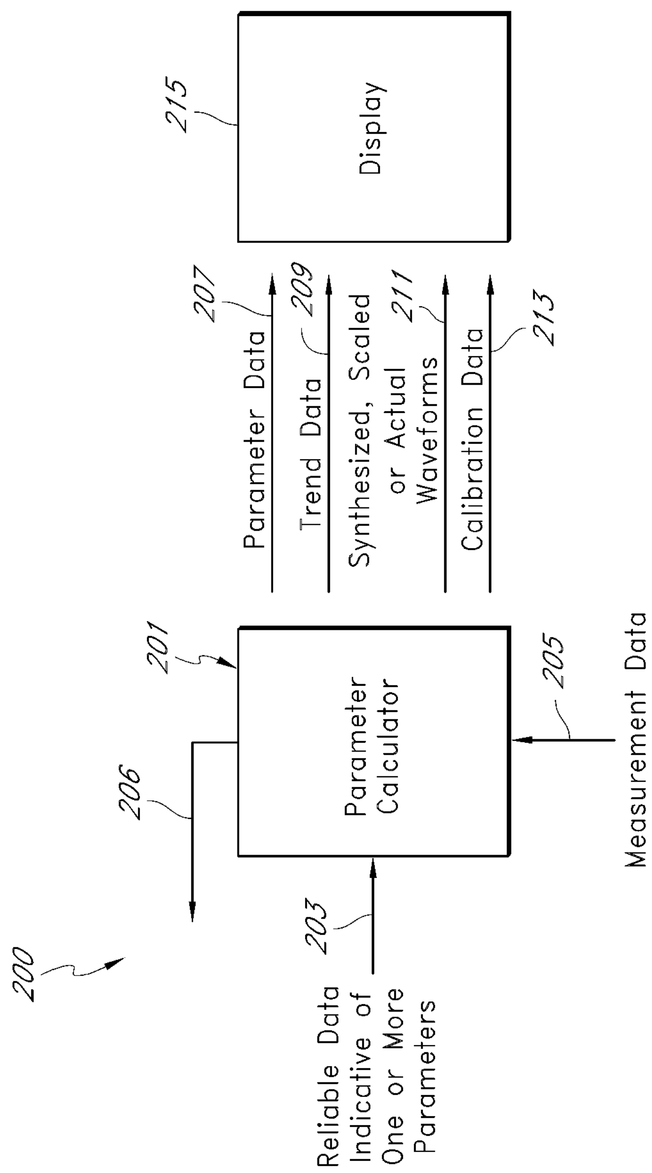
FIG. 2 illustrates a calibration system.

FIG. 2 illustrates a calibration system 200. The calibration system includes a parameter calculator 201. The parameter calculator includes one or more inputs 203 for reliable data indicative of one or more parameters and one or more inputs 205 for measurement data. The reliable data indicative of one or more parameters is communicated from a reliable, often invasive, patient monitor. The measurement data is communicated from a physiological sensor.

The parameter calculator 201 uses the reliable data indicative of one or more parameters to calibrate, if necessary, the measurement data or information derived from the measurement data. Calibration may include modeling, scaling, transforming, finding a best fit, finding a linear fit, filtering, adaptive correlation, cross correlation, or any other calibration steps known to a skilled artisan from the disclosure herein.

The parameter calculator 201 can calculate one or more physiological parameters and output information indicative of that parameter. The parameter calculator 201 may also advantageously calculate trend data and synthesize or scale waveform data. The parameter calculator 201 includes one or more outputs, such as, for example, parameter data output 207, trend data output 209, synthesized, scaled, or actual waveform output 211, or calibration data output 213. The parameter data output 207 communicates data indicative of one or more physiological measurements. The trend data output 209 communicates data indicative of trend information for the one or more physiological measurements. The synthesized, scaled, or actual waveform data output 211 communications waveform data which has been synthesized, scaled, or unaltered. The calibration data output 213 communicates information related to calibrations performed by the parameter calculator 201. The outputs 207, 209, 211, 213 can communicate with display 215, a separate patient monitoring device, or other device configured to receiving physiological parameter information.

In an embodiment, the parameter calculator 201 is included within a single device. In an embodiment, the parameter calculator 201 is included within several separate devices. In an embodiment, the parameter calculator 201 comprises a processor, processor board, or OEM board. In an embodiment, the parameter calculator 201 is portable. In an embodiment, the parameter calculator 201 comprises a desktop parameter calculator. Data communicated between the various components of the calibration system can be communicated through cables or wirelessly. A skilled artisan will also understand from the disclosure herein, that other inputs and/or outputs can be included with the system of the present disclosure. For example, an error data output can be used to communicate the error calculated between the measured data and the reliable data.

Figure 3:
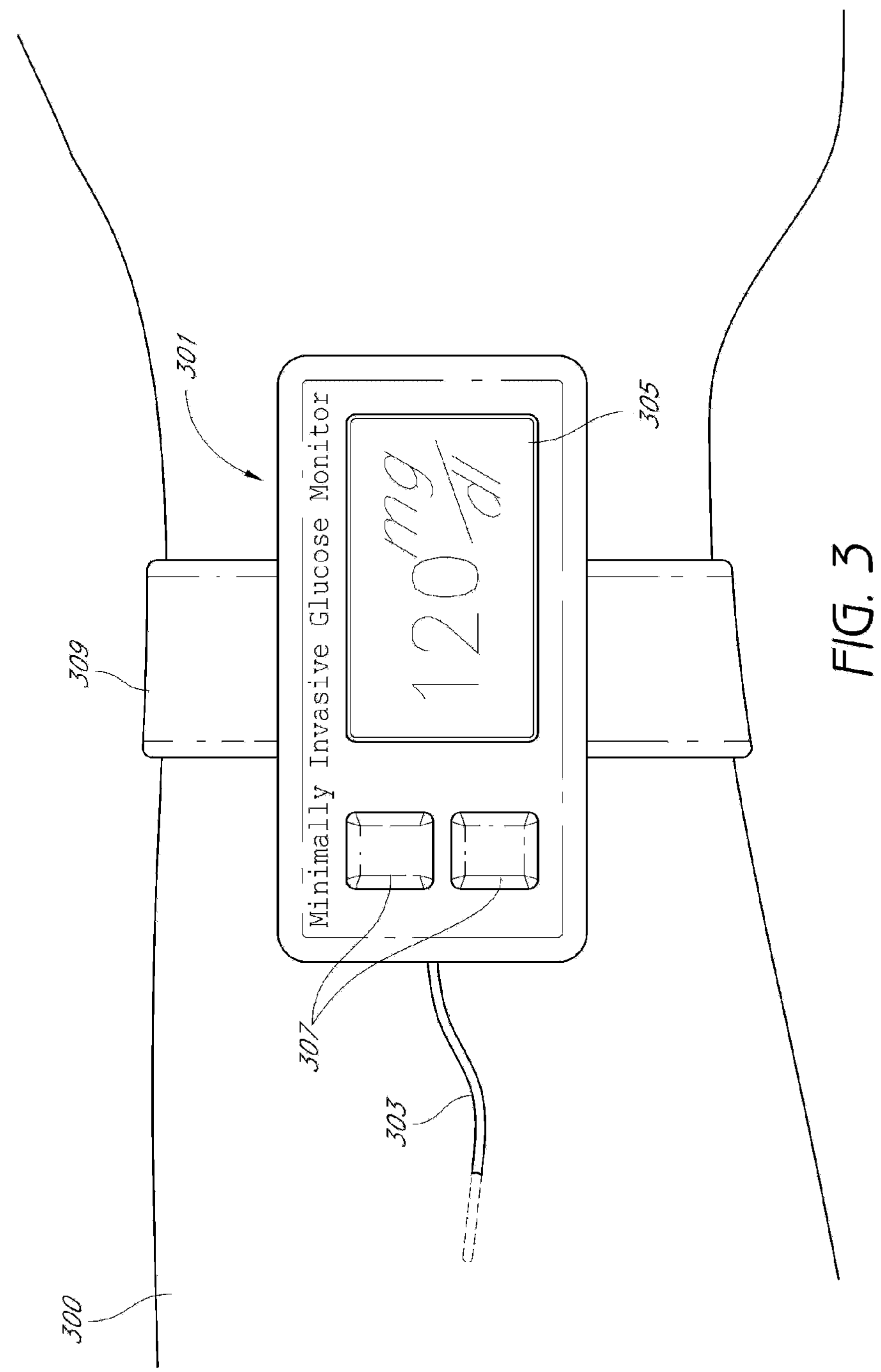
FIG. 3 illustrates a minimally invasive glucose monitor.

FIG. 3 illustrates an embodiment of a minimally invasive glucose monitor. As illustrated, a minimally invasive glucose monitor 301 is attached to a patient 300. The minimally invasive glucose monitor 301 includes a probe 303 which is inserted into the body, often just beneath the skin. The probe 303 measures glucose levels in the patient 300. The probe 303 communicates the measurements to the minimally invasive glucose monitor 301. In an embodiment, the probe 303 is attached to the monitor 301. In an embodiment, the probe is separate from the monitor 301. In an embodiment, the probe 303 communicates through a cable connection with the monitor 301. In an embodiment, the probe 303 communicates wirelessly with monitor 301. In an embodiment, the monitor 301 is attached to the patient 300 by attachment piece 309. In an embodiment, the monitor 301 includes a display 305. In an embodiment, the monitor includes one or more buttons 307.

In operation, the minimally invasive glucose monitor 301 continuously, nearly continuously, or intermittently (periodically or otherwise) measures blood glucose using probe 303. The probe detects glucose levels present in the body and communicates the glucose levels to the minimally invasive glucose monitor 301. The minimally invasive glucose monitor 301 calculates the patient's glucose level based upon information acquired from probe 105. Examples of a minimally invasive glucose monitor and probe are described in U.S. Pat. No. 6,613,379, entitled "Implantable Analyte Sensor," issued to Ward et al., and U.S. Pat. No. 6,695,860, entitled "Transcutaneous Sensor Insertion Device," also issued to Ward et al, the entire contents of both of which are herein incorporated by reference.

Figure 4:
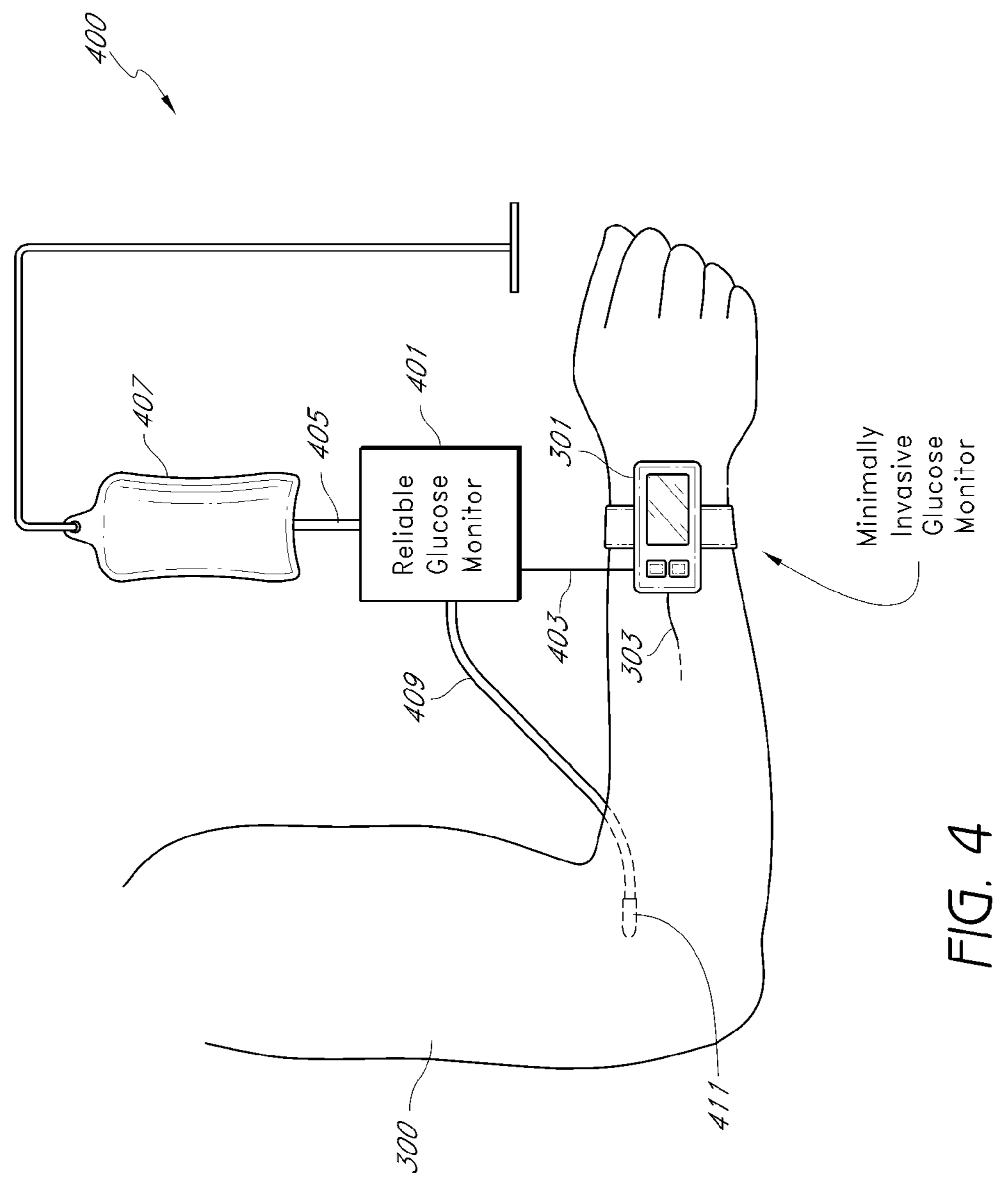
FIG. 4 illustrates a glucose calibration system.

FIG. 4 illustrates an embodiment of a glucose calibration system. For example, the glucose level of a patient 300 is measured by a minimally invasive glucose monitor 301. As described above, the minimally invasive glucose monitor 301 includes a probe 303 inserted into the patient 300 for measuring glucose levels. The glucose level of patient 300 is also measured by a reliable glucose monitor 401. The reliable glucose monitor 401 communicates data indicative of glucose levels in patent 300 to the minimally invasive glucose monitor 201. The minimally invasive glucose monitor 301 uses the communicated reliable data indicative of glucose levels in patient 300 to calibrate glucose information communicated by probe 303.

In an embodiment, the reliable glucose monitor 401 communicates with the minimally invasive glucose monitor 301 through a cable or a wireless connection. In an embodiment, the reliable glucose monitor 401 and the minimally invasive glucose monitor 301 communicate with a separate calibration unit either through a cable or wirelessly. In an embodiment, the minimally invasive glucose monitor 301 communicates with the reliable glucose monitor 401. In an embodiment, the minimally invasive glucose monitor 301 communicates a command to take a measurement to the reliable glucose monitor 401.

In an embodiment, the reliable glucose monitor 401 is operably connected to an IV line 409. The IV line 409 is operably connected to a catheter 411 which is inserted into a vein of the patient 300. The reliable glucose monitor 401 is also operably connected to an IV line 405 which is operably connected to an fluid bag 407. In operation, the reliable glucose monitor 401 intermittently draws blood from patient 300 through catheter 411 and IV line 409 and tests the blood for glucose levels. When the reliable glucose monitor 401 is not drawing blood from the patient 300, it supplies fluid to the patient 300 from fluid bag 407 and IV line 405 through IV line 409 and catheter 411. In an embodiment, the reliable glucose monitor 401 uses glucose test strips to measure glucose levels in the blood. In an embodiment, the reliable glucose monitor 401 uses chemicals analyses to test the glucose levels.

In an embodiment, the reliable glucose monitor 401 is programmed to take measurements at predetermined intervals. In an embodiment, the measurements are taken in intervals of about 5 minutes to about 12 hours. In an embodiment, the measurements are taken in intervals of about 5 minutes to about 10 minutes. In an embodiment, the measurements are taken in intervals of about 1 to about 2 hours. In an embodiment, the measurement intervals are dynamically determined based on calibration feedback as described below. In an embodiment, the minimally invasive glucose monitor 301, or another intermediary device communicate a take measurement command to the reliable glucose monitor. In an embodiment, the minimally invasive or intermediary device communicate a take measurement command in predetermined or dynamically determined intervals as described above.

Figure 4A:
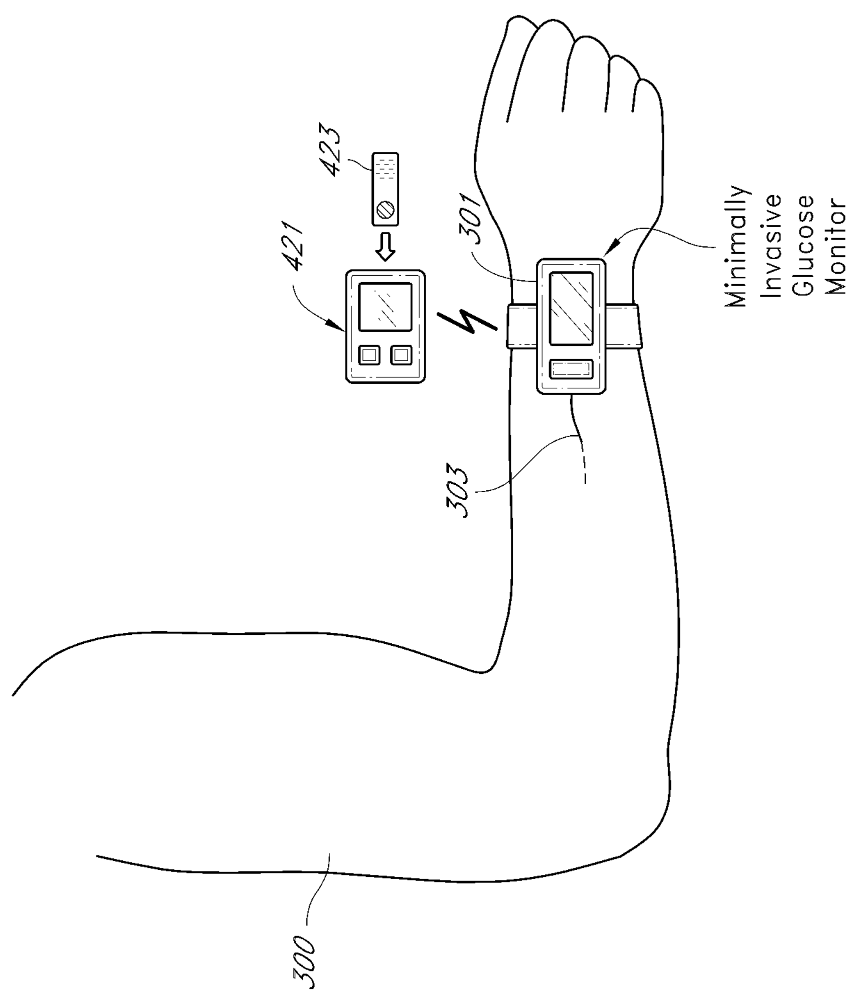
FIG. 4A illustrates another embodiment of a glucose calibration system.

FIG. 4A illustrates another embodiment of a glucose calibration system in which glucose test strips and a glucose test meter are used to measure glucose levels. A user uses the glucose test strips and glucose test meter to measure glucose levels. Once measured, the glucose test meter communicates the glucose levels to the minimally invasive glucose meter for calibration.

Figure 4B:
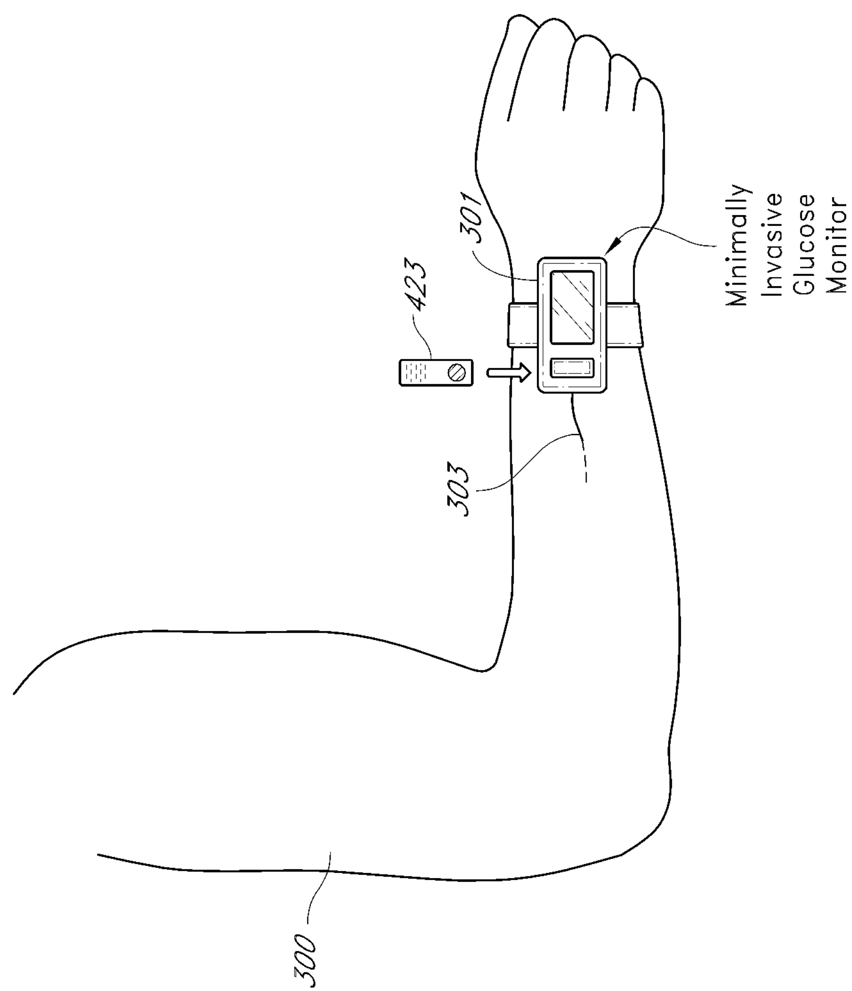
FIG. 4B illustrates yet another embodiment of a glucose calibration system.

FIG. 4B illustrates yet another embodiment of a glucose calibration system. In this embodiment, a glucose test meter is incorporated into the minimally invasive glucose monitor. A user uses the glucose test strips in conjunction with the minimally invasive glucose monitor to calibrate the minimally invasive glucose measurements. In an embodiment, the minimally invasive glucose monitor alerts a user that a reliable glucose measurement should be taken for calibration purposes.

Figure 5:
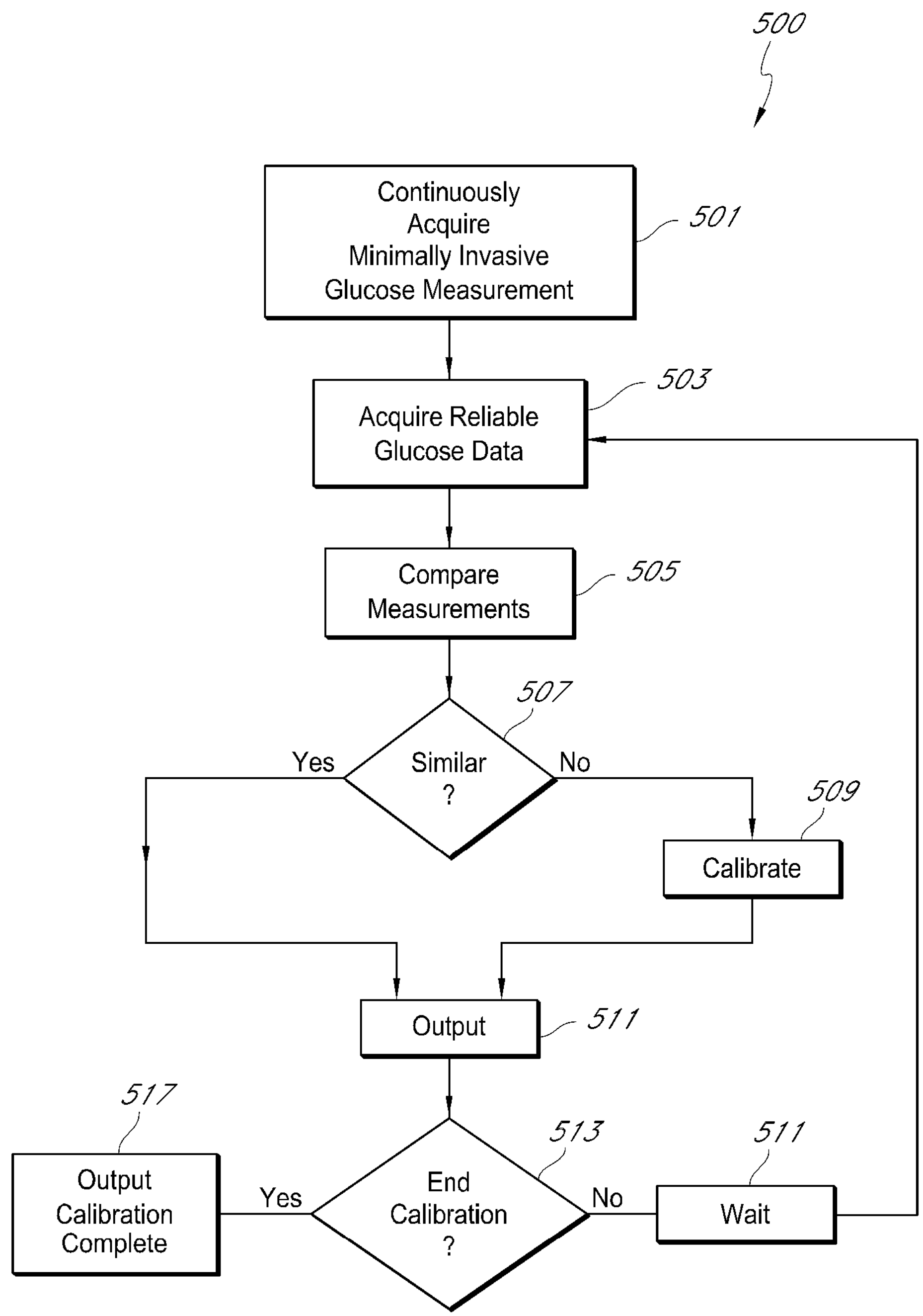
FIG. 5 illustrates a flow chart of an embodiment of a calibration system.

FIG. 5 illustrates a flow chart of an embodiment of a calibration system. The system begins by nearly continuously acquiring minimally invasive glucose measurements at block 501. The system then moves on to block 503 where the system acquires reliable glucose data. The system then moves on to block 505, where a calibration module compares the invasive blood glucose measurement to the acquired minimally invasive glucose measurement.

Once the measurements are compared, the system moves on to decision block 507, where the system looks to see if the measurements are the same or similar. Similar being defined herein as within a predetermined threshold. If the acquired minimally invasive measurement is the same or similar to the acquired reliable glucose data, then the system moves on to block 511 where the glucose reading is outputted, either to a display, a patient monitor, or to another device. If the minimally invasive measurement is not similar, or within a predetermined threshold, then the system moves on to block 509 where the minimally invasive measurements are calibrated. Once calibration is complete, the system moves on to block 511 where the glucose reading is outputted. The system then moves to block 513, where the system decides whether or not the calibration period is complete. If the calibration period is not complete, the system moves to block 515 where it waits a predetermined period of time. After the period of time is complete, the system returns to block 503 and repeats the calibration process. If at block 513, the calibration period is completed, then the system moves to block 517 where the system communicates a calibration complete signal.

In an embodiment, the determination of whether the calibration period is complete is based on an averaging of calibration periods required by other minimally invasive monitors. In an embodiment, the determination of whether the calibration period is compete is based on one or more comparisons of the reliable data and the minimally invasive measurement information. In one embodiment, the determination of whether the calibration period is complete is based on an averaging of calibration periods required by other minimally invasive monitors and one or more comparisons of the reliable data and the minimally invasive measurement information.

Figure 6:
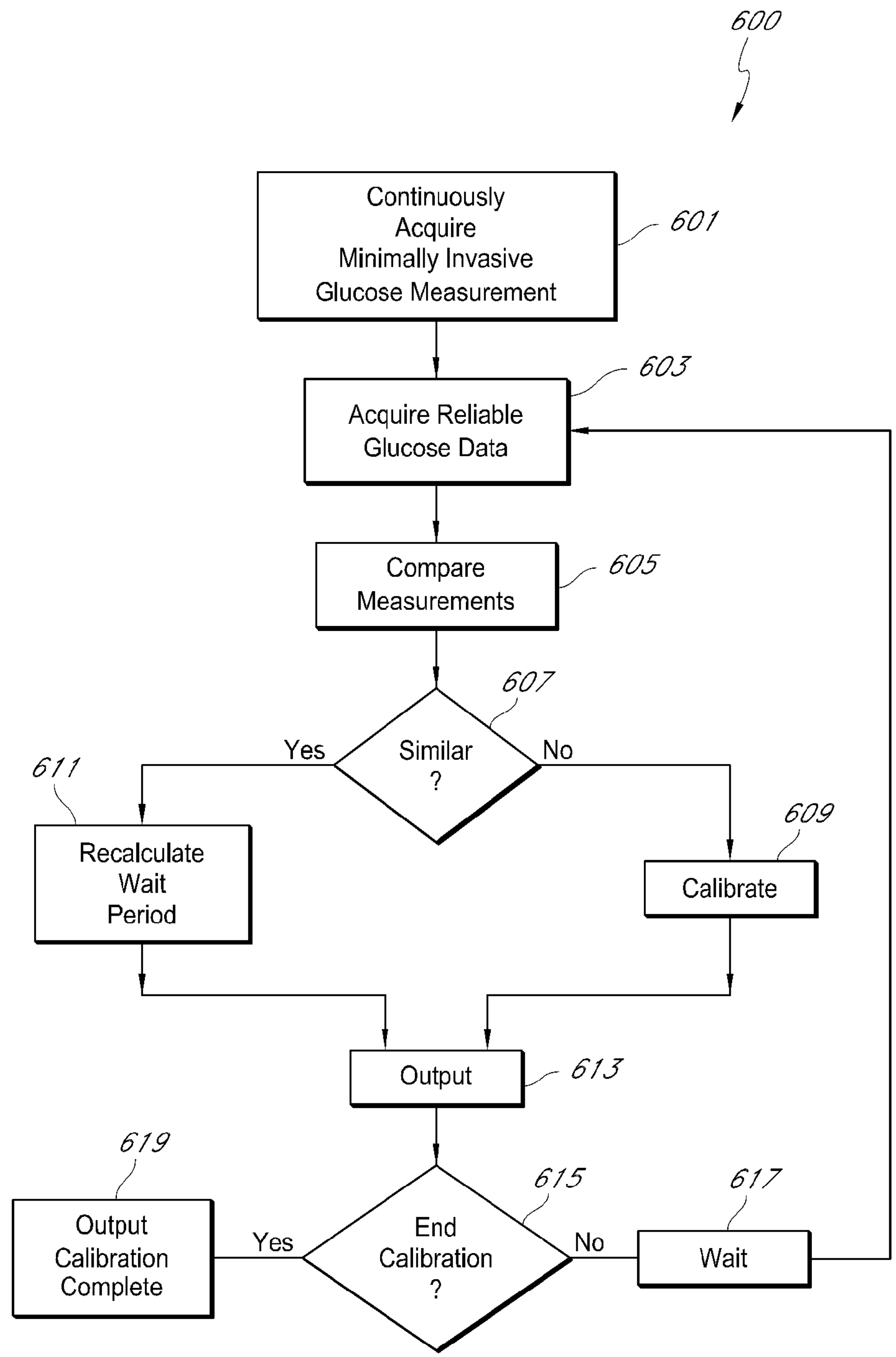
FIG. 6 illustrates a flow chart of another embodiment of a calibration system.

FIG. 6 illustrates a flow chart of another embodiment of a calibration system. The system begins by nearly continuously acquiring minimally invasive glucose measurements at block 601. The system then moves on to block 603 where the system acquires reliable glucose data. The system then moves on to block 605, where a calibration module compares the invasive blood glucose measurement to the acquired minimally invasive glucose measurement.

Once the measurements are compared, the system moves on to decision block 607, where the system looks to see if the measurements are similar. If the acquired minimally invasive measurement is the same or similar to the acquired reliable glucose data, then the system moves on to block 611 where the predetermined wait period of block 617 is recalculated. The recalculation can be based on the number of accurate readings made by the minimally invasive device and/or the accuracy level of the readings made by the minimally invasive device and/or any other parameter which is useful for determining the duration between calibration cycles. The system then moves on to block 613 where the glucose readings are outputted.

If the minimally invasive measurement is not similar, or within a predetermined threshold, then the system moves on to block 609 where the minimally invasive measurements are calibrated. The system then moves on to block 613 where the glucose readings are outputted. Once calibration is complete, the system moves on to block 615, where the system decides whether or not the calibration period is complete. If the calibration period is not complete, the system moves to block 617 where it waits the predetermined period of time, either as initially set or as dynamically recalculated at block 611. After the period of time is complete, the system returns to block 503 and repeats the calibration process. If at block 615, the calibration period is completed, then the system moves to block 619 where the system communicates a calibration complete signal.

Another Example Calibration System

Figure 7:
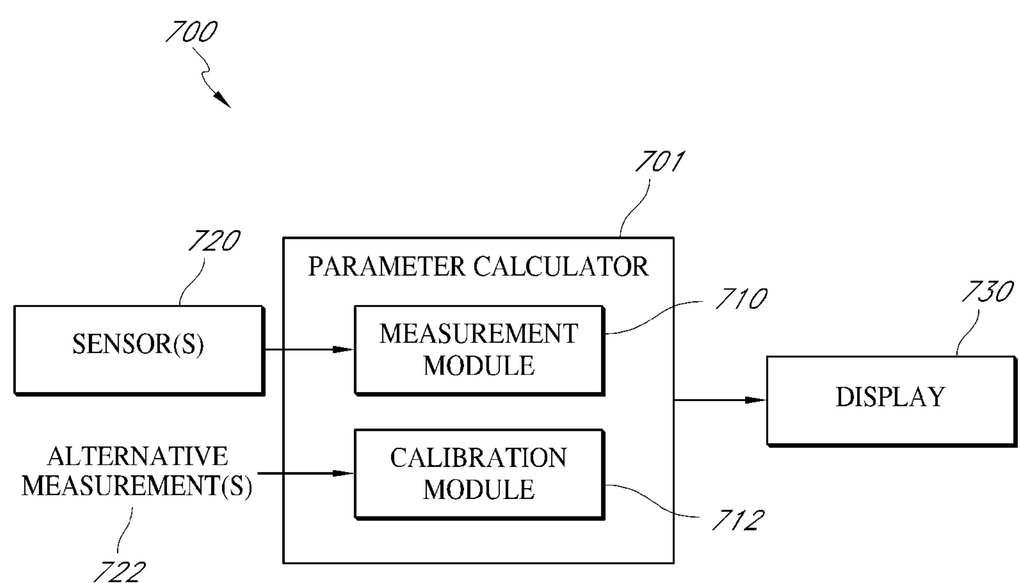
FIG. 7 illustrates another embodiment of a calibration system.

FIG. 7 illustrates another embodiment of a calibration system 700. The calibration system 700 can implement any of the features described above with respect to FIGS. 1 through 6. In addition, the calibration system 700 can implement additional features that can advantageously enable a clinician to compare noninvasive physiological parameter measurements with alternative measurements. The calibration system 700 can enable field calibrations of physiological parameters that can supplement any factory calibration provided during manufacture of the calibration system 700.

The calibration system 700 includes a measurement module 710 and a calibration module 712. Each of these modules 710, 712 can be implemented in hardware and/or software. The measurement module 710 can acquire, receive, or otherwise obtain signals reflecting physiological information from one or more sensors 720. The one or more sensors 720 can be any of the sensors described above or any other physiological sensor(s), including, for example, optical sensors, glucose sensors, pulse oximetry sensors, hemoglobin sensors, dishemoglobin sensors, acoustic sensors, ECG sensors, EEG sensors, and the like.

The measurement module 710 can analyze the physiological information to measure one or more physiological parameters, analytes, or concentrations thereof, including, but not limited to, oxygen saturation ($SpO_2$), total hemoglobin (SpHb), glucose, respiratory rate, and the like. The measurement module 710 can output parameter data, trend data, and/or synthesized, scaled, or actual waveforms, to a display 730 (see FIGS. 9 and 10).

The calibration module 712 receives, acquires, or otherwise obtains an alternative measurement 722. In one embodiment, the alternative measurement is a calibration measurement that enables the calibration module 712 to calibrate one or more of the measurements made by the measurement module 710. The alternative measurement 722 can be an invasive measurement, such as a measurement made in a hospital lab, a minimally-invasive measurement, or the like. As used herein, the term "invasive," in addition to having its ordinary meaning, can also mean minimally-invasive. The alternative measurement 722 can be related to a parameter measured by the measurement module 710. For instance, if the measurement module 710 noninvasively measures hemoglobin of a patient, the alternative measurement 722 can be an invasive measurement for the same patient. The alternative measurement 722 can also be a noninvasive measurement from another noninvasive sensor, or even a different type of noninvasive sensor. Multiple alternative measurements 722 can be input into the calibration module 712.

In one embodiment, the alternative measurement(s) 722 is input into the calibration module 712 by a clinician. The calibration module 712 can expose a user interface for presentation to the clinician (or other user), for example, on the display 730. The user interface can include one or more user interface controls, such as context menus, buttons, or the like that enable the clinician to input the alternative measurement 722. The alternative measurement 722 can also be received from another device, for example, over a network (such as a hospital network, a LAN, a WAN, the Internet, or a combination of the same). The alternative measurement 722 can also be received from a second sensor coupled with a patient.

The calibration module 712 can output the alternative measurement 722 in conjunction with or separate from the measurement(s) obtained by the measurement module 710. In one embodiment, the calibration module 712 outputs a value that reflects the alternative measurement 722 next to, alongside, above, below, or in relation to the measurement obtained by the measurement module 710. The calibration module 712 can output the alternative measurement 722 instead of the noninvasive measurement obtained by the measurement module 710. The calibration module 712 can also average or otherwise combine the noninvasive measurement and the alternative measurement 722. The calibration module 712 can also use the alternative measurement 722 or measurements to adjust a calibration curve corresponding to the noninvasive measurement.

In another embodiment, the calibration module 722 outputs the difference between the alternative measurement 722 and the measurements obtained by the measurement module 710. Further, the alternative measurement 722 can be a value that represents a difference between a noninvasive measurement and a second (e.g., invasive) measurement. Thus, this difference can be input (e.g., by a clinician) into the parameter calculator 701 instead of the actual alternative measurement 722 itself.

Figure 9:
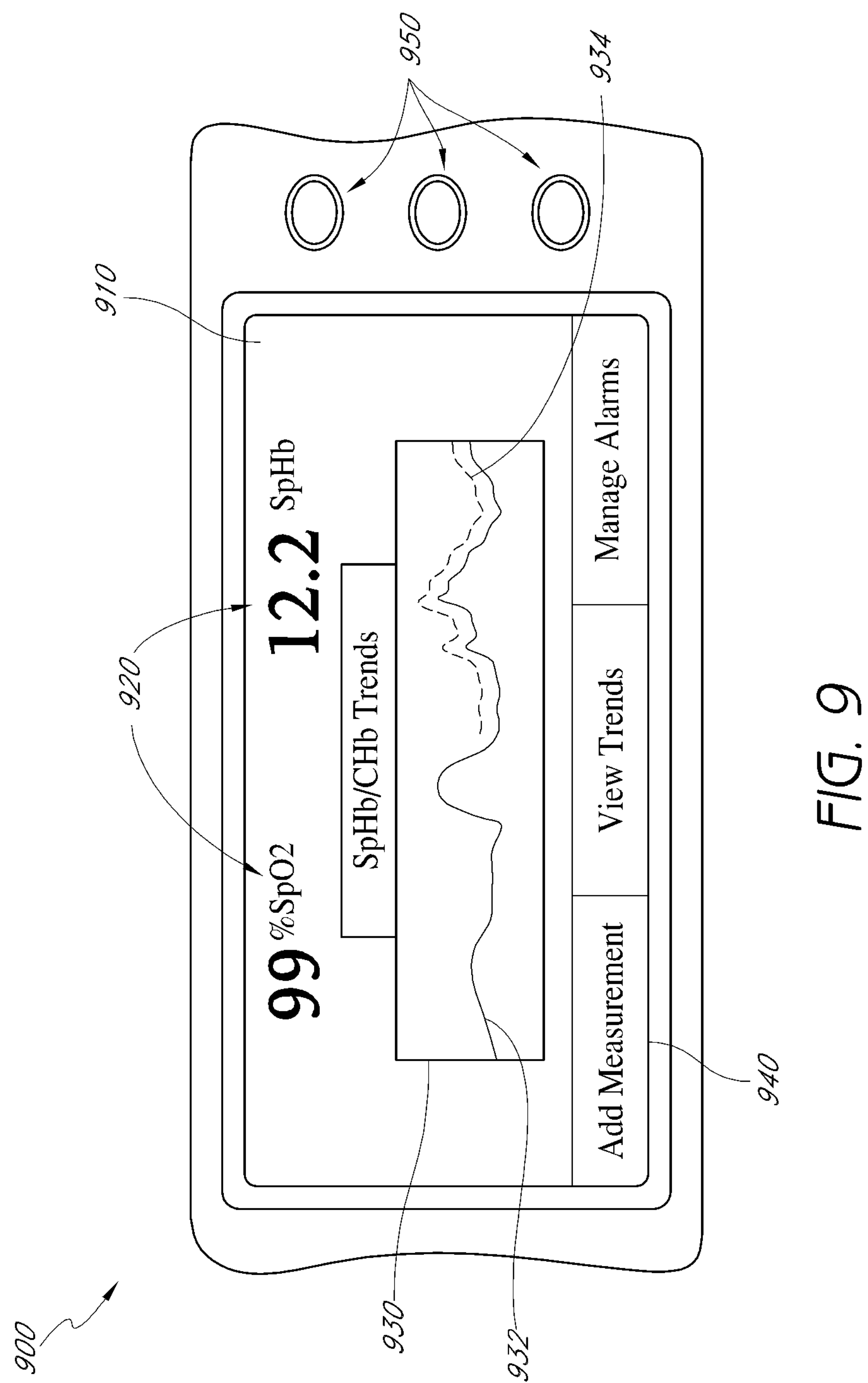
FIGS. 9 through 11 illustrate embodiments of physiological monitor displays.
Figure 10:
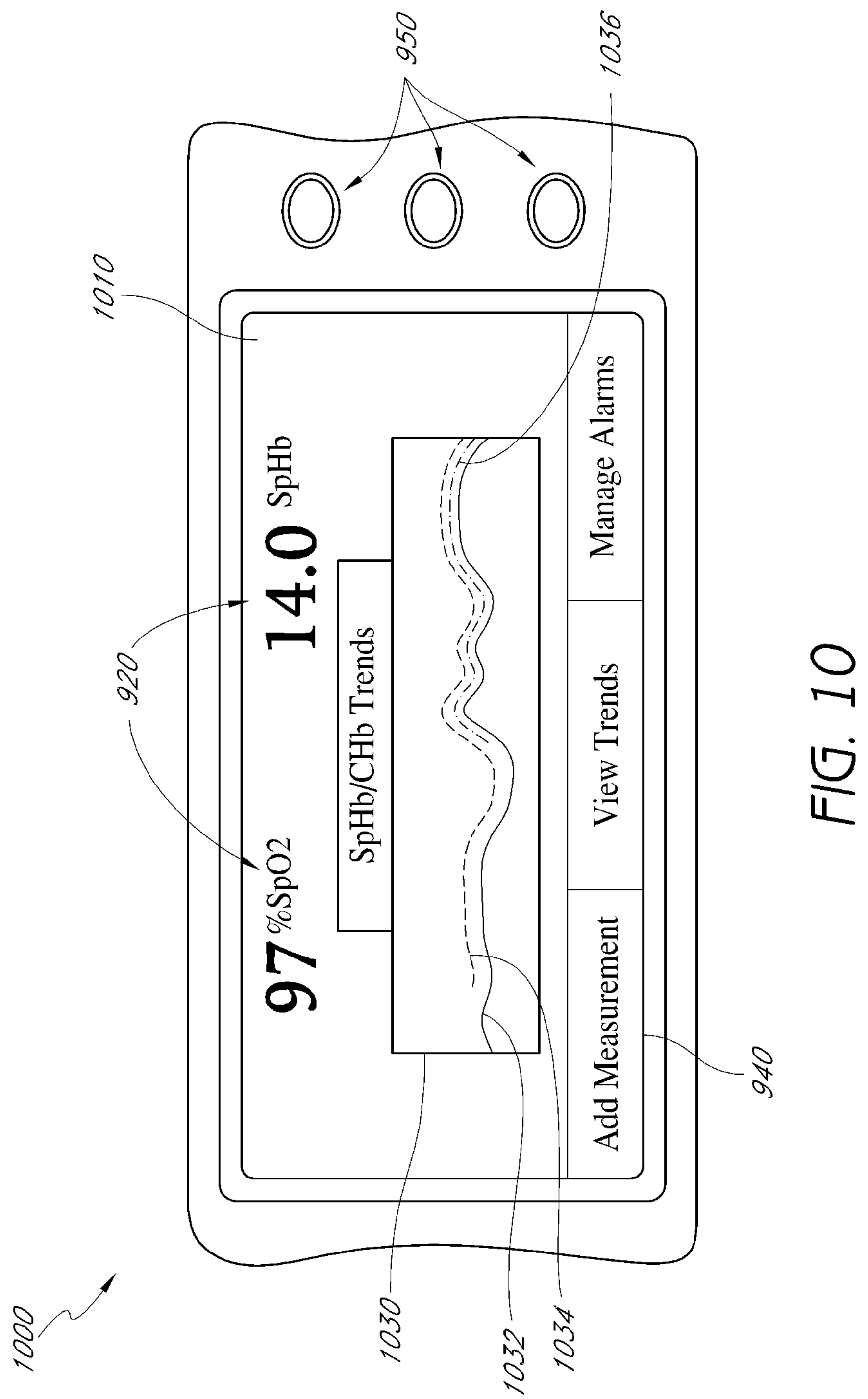

The calibration module 722 can output a trend graph, line, or trend data points that reflect differences between the alternative measurement 722 and the noninvasive measurements over time. This trend graph can be output or overlaid on the same trend graph display output by the measurement module 710. Thus, in certain embodiments, the trend graph or graphs shown on the display 730 can include a trend line (or set of data points) reflecting the noninvasive measurement values together with a trend line (or set of data points) reflecting an offset. The offset can be the difference between the noninvasive measurement values and the alternative measurement value 722. Examples of such offsets are shown in FIGS. 9 and 10 (described below).

Figure 8:
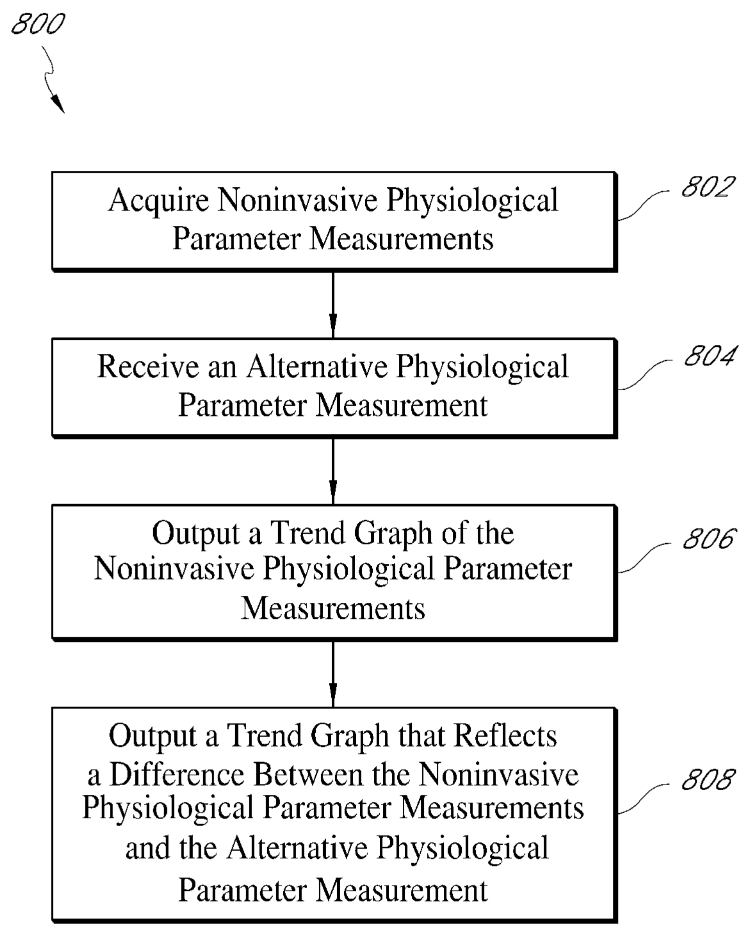
FIG. 8 illustrates a flow chart of an embodiment of a calibration process.

FIG. 8 illustrates a flow chart of an embodiment of a calibration process 800. The calibration process 800 can be implemented by any of the systems or parameter calculators described herein, including the parameter calculator 700. The calibration process 800 enables a physiological monitor to be calibrated, in certain embodiments, by receiving an alternative measurement and displaying the alternative measurement (or an offset derived from that measurement) together with one or more noninvasive measurements.

At block 802, noninvasive physiological parameter measurements are acquired. These measurements can be acquired by the measurement module 710 from a sensor coupled with a patient. At block 804, an alternative physiological parameter measurement is received. This measurement can be received with the calibration module 720, as described above.

At block 806, a trend graph of the noninvasive physiological parameter measurements is output. A second trend graph is output at block 808. This second trend graph reflects a difference between the noninvasive physiological parameter measurements and the alternative physiological parameter measurement. If desired (e.g., by a clinician), the process 800 can be repeated to acquire multiple alternative measurements and to display these alternative measurements as trends together with a trend of the noninvasive measurements.

FIGS. 9 and 10 illustrate embodiments of physiological monitors 900, 1000 having parameter displays 910, 1010. The displays 910, 1010 include several features in the depicted embodiment, including parameter values 920, trend graphs 930, 1030, and a measurement input button 940. The measurement input 940 is an example of a user interface control that provides functionality for a clinician or other user to input one or more alternative measurements. Additional buttons 950 located on the physiological monitor 900 can control a variety of other tasks. The features shown in FIGS. 9 and 10 can be implemented by the calibration module 712 described above.

Referring specifically to FIG. 9, the trend graph 930 includes a measurement waveform 932 and an offset waveform 934. The measurement waveform 932 is an example trend graph for a noninvasive physiological parameter, representing values of that parameter for a given patient over time. The offset waveform 934 is an example trend graph that is offset or biased from the trend graph 932. The offset waveform 934 can represent the difference between noninvasive physiological measurements and an alternative physiological measurement. In one embodiment, the offset waveform 934 is displayed on the trend graph 930 in response to an alternative measurement being entered using the button 940. In the depicted embodiment, the measurement waveform 932 represents SpHb, or hemoglobin, values, and the offset waveform 934 represents values derived from a invasive or minimally invasive hemoglobin. The offset waveform 934 is termed CHb, or calibrated hemoglobin, in the display 910.

In one embodiment, the calibration provided by the offset waveform 934 is terminated when a probe or sensor is taken off of the patient. The calibration can therefore be reset in certain embodiments. However, the offset waveform 934 instead may not be terminated when the probe is taken off.

Referring to FIG. 10, the trend graph 1030 includes a measurement waveform 1032 as before and an offset waveform 1034, also as before. However, a second offset waveform 1036 is also shown, which represents an offset or bias obtained from a second alternative measurement. Thus, multiple alternative measurements can be taken and displayed as offsets or biases from the noninvasively-measured parameter values. In one embodiment, an initial alternative measurement is taken at an initial time, such as shortly before, shortly after, or at about the time that the noninvasive measurements commence. Thereafter, a second alternative measurement is taken partway through a monitoring session (such as a hospital stay).

Instead of displaying both offsets from the first and second alternative measurements, the offset from the second alternative measurement can be displayed in place of the first offset once the second alternative measurement is received by the physiological monitor 1000. In another implementation, the offsets from the first and second alternative measurements can be combined, for example, by averaging. In still other embodiments, the first and second alternative measurements can be used to adjust a calibration curve specific to the individual being measured.

Further, the alternative measurement data from many patients can be used to improve factory calibration settings of the physiological monitor. The alternative measurements and/or their offsets can be averaged, for instance, to determine an average offset to be applied to the factory calibration setting. The measurements can be averaged based on type of patient, type of patient condition, age, gender, and so forth.

Figure 11:
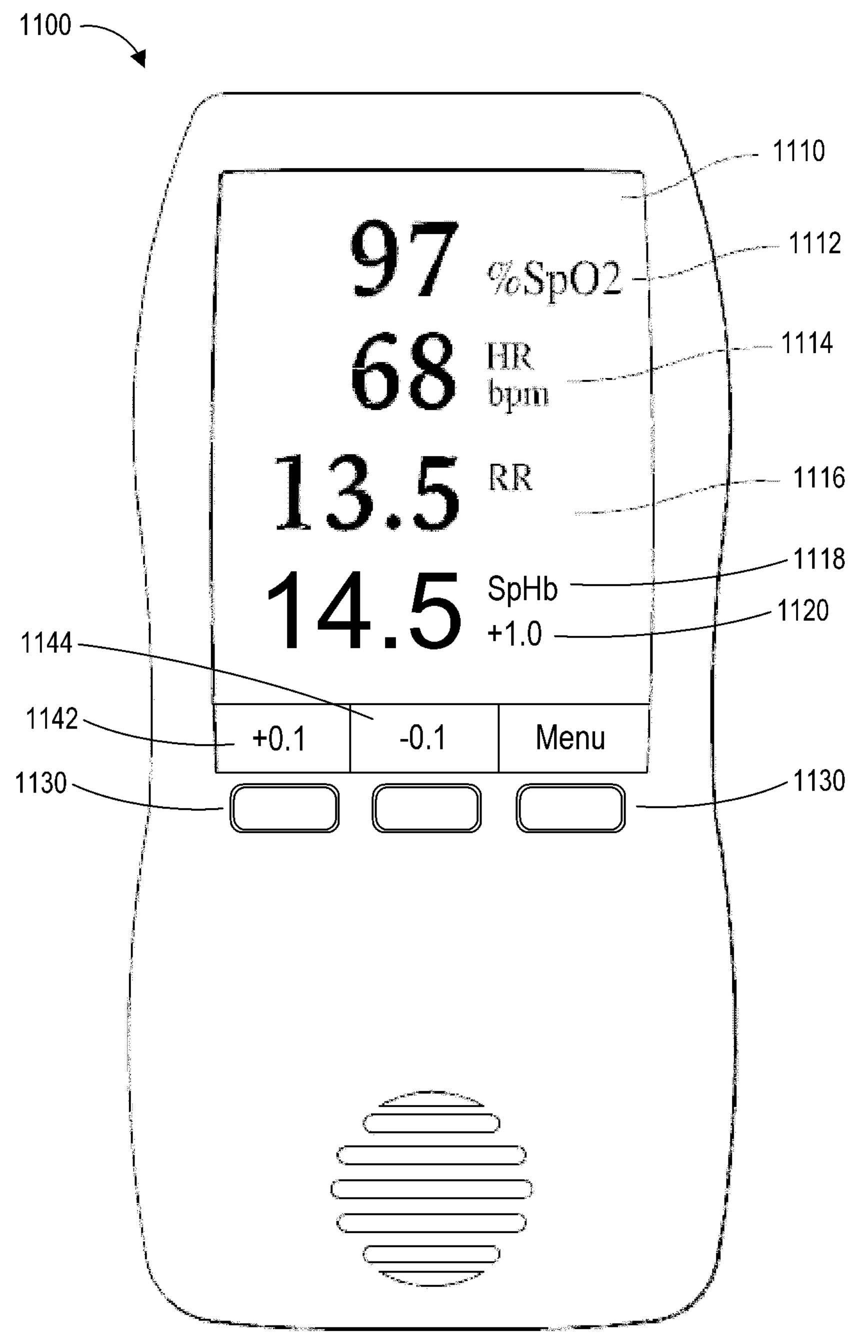

In FIG. 11, another embodiment of a patient monitor 1100 is shown that includes a user interface 1100. The user interface 1100 can be generated at least in part by the calibration module 712. The example user interface 1100 shown outputs parameter values instead of waveforms, including an $SpO_2$ value 1112, a heart rate value 1114, a respiratory rate value 1116, and a noninvasive total hemoglobin value 1118. The parameter values shown in this example are merely examples, and fewer or more parameters can be shown in other implementations.

An offset value 1120 is also shown next to the hemoglobin value 1118. The offset value 1120 can represent a difference between the noninvasive total hemoglobin measurement 1118 and an alternative measurement, such as an invasive or minimally-invasive measurement (or optionally another noninvasive sensor). This offset value 1120 can be used in place of the offset waveforms described above. Of course, in some embodiments, the offset value 1120 can be depicted on a user interface together with an offset waveform. The value of the offset 1120 is "+1.0" in the depicted embodiment. In some embodiments, the offset value 1120 is represented as a positive or negative deviation from the hemoglobin value 1118.

In some embodiments, a clinician or user directly enters the offset value 1120 into the patient monitor 1100. Various types of user interface controls can be used by the clinician or user to input the offset value 1120. As an example, buttons 1130 are shown on the patient monitor 1100 below menu options 1142, 1144 on the user interface 1100. Selection of the appropriate buttons 1130 can cause the offset value 1120 to increase or decrease in value. For purposes of illustration, step values of +0.1 and −0.1 are shown as menu options 1142, 1144. Thus, for example, selection of the +0.1 value via a corresponding button 1130 can cause the offset value 1120 shown to increase by 0.1. The step values shown are merely examples and can vary in different implementations. Further, the step values can be represented as percentages, such as percentage differences from the alternative measurement, in some embodiments.

In other embodiments, the offset value 1120 is communicated to the patient monitor 1100 over a network, for example, from a lab that generates an invasive value or from another computing device. A lab technician or other individual can input the invasive value into a computing system, which then transmits the invasive value to the patient monitor 1100. The patient monitor 1100 can then calculate the difference between a current noninvasive measurement and the invasive value and output this difference as the offset value 1120. In another embodiment, the invasive value received from the lab (or other computing device) has a time stamp associated with it. The patient monitor 1100 may then calculate the offset value 1120 by comparing the invasive value with the noninvasive value that occurred at the same time or a close time to the timestamp of the invasive value.

In other embodiments, the actual alternative measurement is shown in place of or in addition to an offset value 1120. Further, the clinician or user can enter the actual invasive measurement instead of an offset value 1120 in some embodiments. In addition, user interface controls other than buttons, such as touch screen inputs, can be employed to add offset values or alternative measurements.

Other features that may be employed by the patient monitor 1100 can include a feature that displays an indication of the age of the offset value 1120. This feature can include a timestamp of when the value was either obtained (e.g., at the lab) or when the value was input into the patient monitor 1100. The patient monitor 1100 can include further user interface controls that enable a clinician or other user to input the timestamp, or the timestamp can be obtained directly from the lab or other computing device over a network. In another embodiment, the appearance of the offset value 1120 can change to reflect the aging of the offset value 1120. Any of the following display features can equally apply to the parameter value itself (e.g., the hemoglobin value 1118). For instance, the offset value 1120 (or parameter value 1118) can be one color when first entered (such as green) but change to another color (such as red) as the offset value 1120 ages. In another embodiment, the offset value 1120 (or parameter value 1118) blinks with a frequency that depends on the age of the offset value 1120. In another embodiment, the offset value 1120 begins blinking when the age of the offset value 1120 reaches a certain threshold. In yet another embodiment, the offset value 1120 can be reset to a value 0 when a threshold time has passed. Showing the age of the offset value 1120 in any of these ways or using other techniques can assist a clinician in determining the relevancy of the offset value 1120. Age-related techniques may also be implemented using the trend graph user interfaces described above with respect to FIGS. 9 and 10, including blinking, changing color, showing timestamps, and the like.

CONCLUSION

Although the foregoing inventions have been described in terms of certain preferred embodiments, other configurations are possible. For example, an invasive blood pressure monitor can be used to calibrate a non-invasive blood pressure monitor. In addition, various types of physiological monitors can be used to calibrate various other types of physiological monitors. For example, a minimally invasive physiological monitor can be used to calibrate a non-invasive physiological monitor.

The modules described herein of certain embodiments may be implemented as software modules, hardware modules, or a combination thereof. In general, the word "module," as used herein, can refer to logic embodied in hardware or firmware or to a collection of software instructions executable on a processor. Additionally, the modules or components thereof may be implemented in analog circuitry in some embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Depending on the embodiment, certain acts, events, or functions of any of the methods described herein can be performed in a different sequence, can be added, merged, or left out all together (e.g., not all described acts or events are necessary for the practice of the method). Moreover, in certain embodiments, acts or events can be performed concurrently, e.g., through multi-threaded processing, interrupt processing, or multiple processors or processor cores, rather than sequentially.

The various illustrative logical blocks, modules, circuits, and algorithm steps described in connection with the embodiments disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, a hard disk, a removable disk, a CD-ROM, or any other form of computer-readable storage medium known in the art. An exemplary storage medium is coupled to a processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A measurement device comprising:

a measurement module configured to obtain noninvasive physiological parameter measurements from a sensor coupled with a patient; and a calibration module comprising a processor configured to:

receive an alternative physiological parameter measurement at the noninvasive device, output a first trend graph of the noninvasive physiological parameter measurements for display, output a second trend graph that reflects a difference between the noninvasive physiological parameter measurements and the alternative physiological parameter measurement;

determine an offset value based at least in part on the difference between the noninvasive physiological parameter measurements and the alternative physiological parameter measurement;

calibrate the noninvasive device based at least in part on the offset value;

track an age of the offset value over time;

provide a user interface control on the noninvasive device, the user interface control configured to provide functionality for a user to input the offset value into the noninvasive device, the user interface control further configured to provide functionality for the user to modify the offset value over time;

display the offset value on a user display of the noninvasive device; and display an indication of the age of the offset value on the user display.

2. The measurement device of claim 1, wherein the user interface control is further configured to provide functionality for the user to input the alternative physiological parameter measurement into the measurement device.

3. The measurement device of claim 1, wherein the calibration module is further configured to output a third trend graph in response to receiving a second alternative physiological parameter measurement.

4. The measurement device of claim 1, wherein the alternative physiological parameter measurement is an invasive measurement.

5. The measurement device of claim 1, wherein the alternative physiological parameter measurement is a minimally-invasive measurement.

6. The measurement device of claim 1, wherein the alternative physiological parameter measurement is a second non-invasive measurement from a second sensor.

7. The measurement device of claim 1, wherein the sensor measures a hemoglobin parameter.

8. A system for calibrating a measurement device, the system comprising:

a measurement module configured to receive a signal from a physiological sensor, obtain a noninvasive measurement of a physiological parameter responsive to the received signal, and output a value of the noninvasive measurement for presentation to a user; and a calibration module comprising a processor configured to:

receive an input reflecting an invasive measurement value for the physiological parameter;

output an alternative value that reflects the invasive measurement value;

determine an offset value based at least in part on the difference between the noninvasive measurement and the invasive measurement value;

calibrate the noninvasive device based at least in part on the offset value;

track an age of the offset value over time;

provide a user interface control on the noninvasive device, the user interface control configured to provide functionality for the user to input the offset value into the noninvasive device, the user interface control further configured to provide functionality for the user to modify the offset value over time;

display the offset value on a user display of the noninvasive device; and display an indication of the age of the offset value on the user display, wherein at least the calibration module is implemented by one or more processors.

9. The system of claim 8, wherein the alternative value is the offset value.

10. The system of claim 8, wherein the calibration module is further configured to provide functionality for the user to input the invasive measurement value.

11. The system of claim 8, wherein the calibration module is further configured to receive the invasive measurement value over a network.

12. The system of claim 8, wherein the calibration module is further configured to output an indication of an age of the alternative value.

13. The system of claim 8, wherein the physiological parameter is hemoglobin.

14. The system of claim 8, wherein the physiological parameter is glucose.

* * * * *